Figure 1:
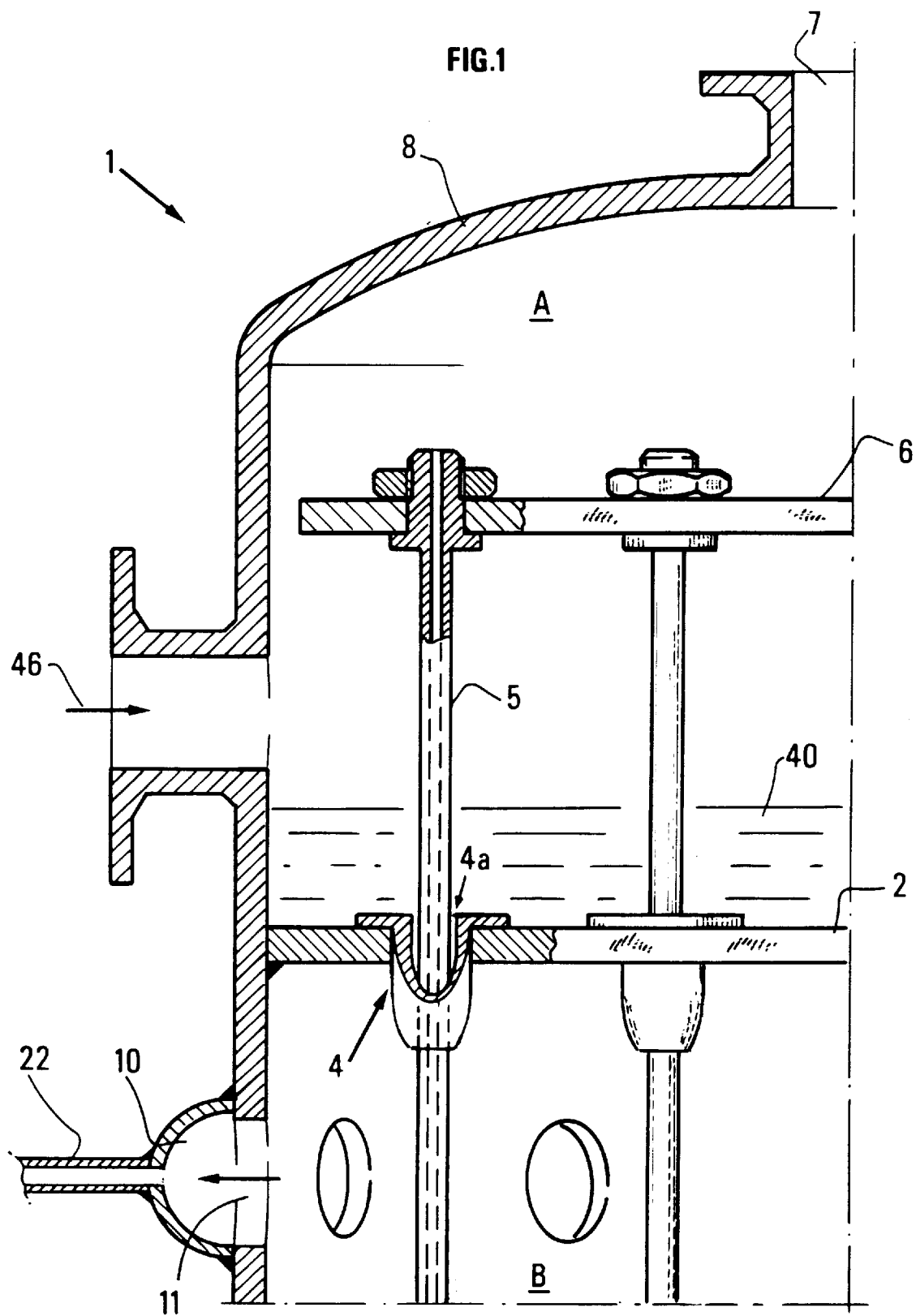

United States Patent [19]
Minkkinen et al.

[11] Patent Number: 6,162,262
[45] Date of Patent: Dec. 19, 2000

[54] DEVICE FOR CRYSTALLIZATION BY ISENTROPIC EXPANSION AND ITS USE

[75] Inventors: Ari Minkkinen, Saint Nom la Breteche; Paul Mikitenko, Noisy le Roy, both of France

[73] Assignee: Institut Francais du Petrole, Rueil Malmaison Cedex, France

[21] Appl. No.: 09/097,684

[22] Filed: Jun. 16, 1998

[30] Foreign Application Priority Data

Jun. 16, 1997 [FR] France .................................. 97 07553

[51] Int. Cl.$^7$ ...................................................... C30B 7/08
[52] U.S. Cl. ........................ 23/295 R; 23/307; 422/245.1
[58] Field of Search ................. 23/295 R, 307; 422/245.1

[56] References Cited

U.S. PATENT DOCUMENTS

| | | | |
|---|---|---|---|
| 4,124,688 | 11/1978 | Shibazaki et al. | 423/432 |
| 4,245,998 | 1/1981 | Okouchi et al. | 422/245.1 |
| 5,401,476 | 3/1995 | Hotier et al. | 422/222 |
| 5,435,155 | 7/1995 | Paradis | 165/135 |
| 5,558,678 | 9/1996 | Weger | 422/245.1 |
| 5,593,496 | 1/1997 | Schranz | 422/245.1 |
| 5,662,870 | 9/1997 | Walsh | 422/245.1 |

FOREIGN PATENT DOCUMENTS

| | | |
|---|---|---|
| 0455243 | 11/1991 | European Pat. Off. . |
| 06115889 | 8/1994 | European Pat. Off. . |
| 972036 | 5/1959 | Germany . |
| 2222755 | 11/1973 | Germany . |
| WO 96/20908 | 7/1996 | WIPO . |
| WO 96/22262 | 7/1996 | WIPO . |

*Primary Examiner*—Robert Kunemund
*Attorney, Agent, or Firm*—Millen White Zelano & Branigan

[57] ABSTRACT

Device and process for crystallizing a component, e.g. paraxylene, from a mixture that comprises a chamber (1) that has in its upper part means (46) for supplying the mixture, collecting means (20), and in its lower part, crystals of the component in suspension in a mother liquor, connected to means (C) for separation and purification of the crystals that are obtained, means (9) for supplying a cold gaseous fluid and means (22) for drawing off the so-called hot gaseous fluid that results from the direct heat exchange, whereby said device also comprises means for shaping a descending flow of the mixture onto tubes such that the cold gaseous fluid that circulates upward exchanges cold directly with the mixture, whereby means (22) for drawing off the hot gaseous fluid are connected to at least one fluid recompression means (24b), whose output is connected to at least one heat exchanger (27), whereby the heat exchanger is connected to a turbo-expander (30), which is connected to means (31) for supplying cold gaseous fluid.

26 Claims, 2 Drawing Sheets

DEVICE FOR CRYSTALLIZATION BY ISENTROPIC EXPANSION AND ITS USE

FIELD OF THE INVENTION

The invention relates to a device for crystallizing a component from a liquid mixture that contains it, and its use particularly for separating paraxylene from a hydrocarbon mixture that contains aromatic isomers with 8 carbon atoms.

The invention also applies very particularly to the purification to 99.9%, for example, of paraxylene for the preparation of terephthalic acid, an intermediate petrochemical for the synthesis of textile fibers.

BACKGROUND OF THE INVENTION

Among the previous processes that are suitable for the purification of paraxylene, crystallization is the one that has been used most, even though it is limited by a low recovery level due to the existence of a eutectic whose paraxylene concentration in the mixture reaches about 10 to 13%.

With the development of techniques for separation by adsorption in a molecular sieve, it is possible to achieve an excellent paraxylene yield, greater than, for example, 98%, independently of the eutectic composition limitation.

Usually, a recovery in excess of 98% of paraxylene is obtained with the processes of a simulated countercurrent fluid bed (U.S. Pat. No. 2,985,589) when the purity of the product is close to 95% by weight. A higher purity, exceeding 99%, however, can be reached at the expense of the yield.

Since an adsorption process makes it possible to carry out the separation of paraxylene with a high yield at the expense of purity while a crystallization process makes it possible to obtain a more pure product to the detriment of the yield, a hybrid process has been proposed that combines adsorption in a molecular sieve of aromatic $C_8$ isomers, followed by crystallization of the paraxylene-enriched fraction (U.S. Pat. No. 5,401,476, and EP-B.531191 that are incorporated as references).

This process thus combines the advantages of a high yield and a very high purity of the wanted product compared to the processes of adsorption or of crystallization used separately.

Furthermore, the technology of crystallization is very old and has hardly been updated, considering the industrial breakthrough of the adsorption process in the simulated fluid bed.

The technological background is illustrated by the following documents: EP-A 611 589, EP-A 455 243, DE-A 2 222 755 and DE-C 972 036.

Crystallization for separating the paraxylene from a mixture of xylenes is generally carried out at very low temperatures, located in the range of those that can be attained by refrigeration with ethane or with ethylene. The costs of refrigeration and the consumption of energy are high, particularly because it is necessary to produce a cascade of cold cycles, with intermediate refrigeration with propane or with propene.

Certainly, this consumption is reduced when the operation is carried out in a higher range of crystallization temperatures, +10 to −30° C., for example, as is the case when the crystallization feedstock is enriched to more than 50%, for example, preferably with more than 70% paraxylene, by an enrichment process by adsorption of xylenes or by paraselective dismutation of toluene, for example.

Moreover, the process of continuous crystallization by indirect exchange generally requires that the exchangers be scraped, which is an operation that is delicate and energy-intensive, regardless of the selected cooling level.

SUMMARY OF THE INVENTION

One of the objects of the invention is to remedy the drawbacks that are mentioned above.

Another object is to propose a crystallization technique by direct exchange of kilogram calories with a feedstock which is simpler and easier to use.

Another object is the use of a process of crystallization and a device that correspond, at any desired level of cooling temperature and at very much the same operating expense, knowing, of course, that the power of the gas compressors will depend on the desired cooling temperature.

It has therefore been observed that it was possible to crystallize a product in a liquid mixture that contains it, constituting the crystallization feedstock, by direct exchange of cold with a cold cryogenic gas that is obtained by approximately isentropic expansion of this gas, under very favorable and very economical conditions.

Described more specifically is a device for crystallization of a component from a liquid mixture that contains it and that comprises an elongated chamber that has in its upper part means for supplying said mixture, collecting means, and in its lower part, crystals of the component in suspension in a mother liquor, connected to means for separation and for purification of the crystals that are obtained, means for supplying a cold gaseous fluid that is introduced at at least one point in the lower part of the chamber and means for drawing off the so-called hot gaseous fluid that is placed at the upper part of the chamber, resulting from the direct countercurrent heat exchange of the cold gaseous fluid with the mixture, whereby said device also comprises means for suitable shaping of a descending flow of the mixture such that the cold gaseous fluid that circulates upward exchanges directly from the cold with the mixture that is shaped, whereby the means for drawing off the hot gaseous fluid are connected to at least one fluid recompression means (24b), whereby the recompression means has an output that is connected to at least one heat exchanger, whereby the heat exchanger has an output that is connected to a turbo-expander (30), and whereby the turbo-expander has an output that is connected to cold gaseous fluid supply means (31).

According to an embodiment of the device, the means for suitable shaping of the descending flow of the mixture comprise at least one sprayer that is suitable for forming droplets of the mixture measuring between 50 and 500 micrometers and preferably according to the distribution of sizes of 150 to 200 micrometers for at least 80% of the droplets.

According to another embodiment of the device, the chamber can contain a large number of filaments that are suspended, non-contiguous, and approximately parallel to its longitudinal axis, supported by attachment means that are placed in the vicinity of, for example, the upper end of the chamber and that occupy approximately the entire section of the chamber.

The sprayer that is mentioned above shapes the droplets of the mixture that constitutes the feedstock, which can be deposited on the filaments in the form of a thin film which is subjected to crystallization by direct contact with the cold gas that rises into the crystallization chamber.

These vertical filaments can be hollow, tubes, for example, to lighten the device and/or to make possible the circulation of a hot fluid that reheats that wall of the filament to promote the presence of a liquid film on the latter and the downtake of the crystals into the lower part of the crystallization chamber.

This hot fluid can be a portion of the gaseous fluid that is recovered from the crystallization chamber and recompressed.

According to a variant, the flowing of the liquid mixture onto the filaments can be carried out differently.

Actually, the means for suitable shaping of the flow comprise a chamber for communication with said means for supplying the mixture that comprise a large number of flow orifices that are pierced on the lower transverse wall of the chamber and are equal in number to that of the filaments, whereby each filament passes through an orifice whose surface area is larger than that of the section of the filament, whereby said chamber contains a volume of mixture such that the height of the mixture, in combination with the available flow surface between the orifice and the filament, makes it possible to wet the filament and to ensure a suitable flow of mixture on the surface of each filament.

It may be advantageous to insert an annular sleeve that is made of an inert material into components of the feedstock, not fluidtight, that work with the chamber at each orifice and each filament to carry out the wetting of the filament and the suitable flowing of the feedstock onto the filament.

The feedstock flow rate that flows onto the filaments is thus adjusted in combination with the height of the liquid in the chamber, which itself is controlled by a level probe or a measurement of hydrostatic pressure.

The number of filaments is determined based on the desired exchange surface.

The interaxial distance between two filaments can be equal to at least twice the diameter of the filament.

The flow of the fluids that are present is thus promoted, and bringing the latter into contact can be improved by promoting turbulence, at filaments by known suitable means, as a surface treatment for the filaments.

To facilitate the descent of the crystals, it may be advantageous to connect vibration means, ultrasonic, for, example, to means for attaching filaments.

The invention also relates to a process for using the crystallization device for separation of, for example, paraxylene from a mixture of hydrocarbons that contains aromatic isomers with 8 carbon atoms.

This feedstock can be an isomer mixture that corresponds to the composition of a C8 effluent fraction for catalytic reforming or isomerization of xylenes which will require crystallization at very low temperature (−70° C., for example), if the maximum yield of paraxylene is desired.

The crystallization feedstock can also be a feedstock that contains at least 60% paraxylene and that results from enrichment by adsorption on a molecular sieve in a simulated fluid bed or coming from a selective dismutation of toluene.

In a more detailed manner, the process for using the crystallization device includes the following stages:
preferably approximately isentropic expansion of a gas that is compressed to an initial pressure and is precooled to a suitable temperature T is carried out, whereby the gas is selected from the group that is formed by air, hydrogen, nitrogen and helium, so that the gas has a temperature that is at least 10° C., and preferably 20 to 50° C., lower than the temperature that is desired upon its intake into the crystallization zone, defined based on the purity of the hydrocarbon feedstock and the yield of the crystallization, the expanded gas and cold are introduced at at least one point in the lower part of the crystallization zone, the hydrocarbon feedstock is adequately introduced into the upper part of the crystallization zone, the cold countercurrent gas is brought into direct contact with the hydrocarbon feedstock, a suspension of paraxylene crystals is recovered in a mother liquor in the lower part of the crystallization zone, and hot gas is recovered in the upper part of the crystallization zone, the hot gas is recompressed at a suitable pressure, approximately equal to the initial pressure, it is cooled at least in part to temperature T, the crystals of the mother liquor are separated, and the paraxylene crystals are recovered.

Quite obviously, the recovered crystals are washed and purified according to known techniques, for example, in a countercurrent washing column.

This washing stage can be preceded by a stage where the temperature of the crystals that are obtained rises; this makes it possible to homogenize the size of the crystals and to make the crystallization device and purification device operate at their optimum temperatures, which are very different, as is described in Patent Application WO 96/22262.

The feedstock can be introduced by spraying it into the upper part of the crystallization zone, in the form of droplets of 50 to 500 micrometers. As has been stated, the crystallization zone can contain a large number of filaments. The feedstock can also be introduced at a controlled rate, in the form of a film on said filaments with calibrated orifices on the lower wall of the chamber through which these filaments pass.

According to a characteristic of the process, the hot recompressed gas can be cooled to a temperature that is usually between −30 and +70° C., advantageously between 20 and 50° C., and it can then be expanded at a ratio of 1.5 to 5 relative to the initial pressure, which is the recompression pressure.

The temperature level before the expansion of the gas and the drop in pressure of a gas are determined in relation to the desired cold temperature level in the crystallizer.

According to another characteristic, it is possible to expand the gas at a pressure of 1 at 15 bar and preferably 4 to 8 bar.

Figure 2:
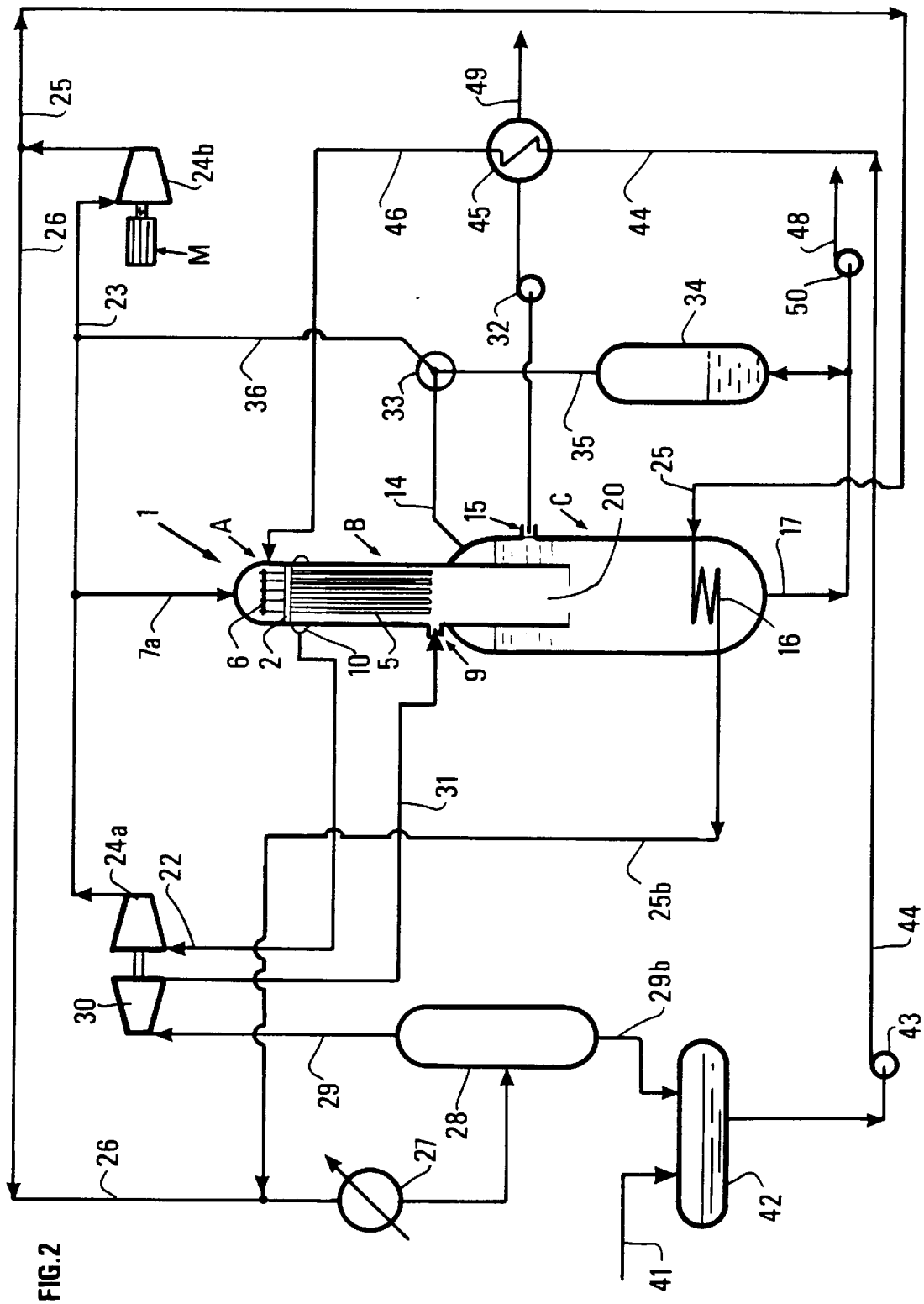

The invention will be better understood based on the following figures that diagrammatically illustrate the device, among which:

FIG. 1 presents a longitudinal section of the upper part of the crystallizer; and FIG. 2 shows an arrangement of the cold chain combined with an advantageous embodiment of the crystallizer.

According to FIGS. 1 and 2, crystallization chamber 1, which has an approximately tubular and vertical shape, comprises three zones A, B, and C:

Zone A is a zone for supply and distribution of the liquid feedstock, zone B is a zone for cooling by direct contact of a cold gas with the filaments that are wetted by the feedstock, zone C is a zone for decanting the suspension of crystals that are obtained in zone B for maturing and purifying these crystals.

In zone A, a liquid feedstock that contains a mixture of xylenes that is preferably precooled so that its temperature approaches its initial crystallization temperature while remaining above it is introduced via a line (46) into a supply chamber (40) with level monitoring. A lower transverse wall (2) of this chamber, which is penetrated by a vast number of orifices (4a) according to a, for example, triangular pitch is welded to an inner wall of chamber 1.

Each orifice comprises an annular, elastic sleeve (4) that is resistant to xylenes.

A sheaf of tubular aluminum filaments (5), suspended by its upper end to a floating head (6), whose number of tubes equals that of the orifices, passes through wall (2) of the chamber through the orifices and, because of the elastic sleeve which partially obstructs the annular space between the filament and the orifice, a liquid film circulates in each filament from top to bottom, at a controlled flow rate. These filaments are placed approximately along the axis of the chamber. An optional stream of hot gas ($N_2$, for example) can be introduced owing to orifice (7) and a line (7a), which are connected to a hot gas source (line 23) in zone A for distributing the feedstock for at least partially reheating the inside of the tubular filaments. Furthermore, it contributes to the flow monitoring of the liquid film. Floating suspension bar (6) is suspended at head (8) of the chamber that contains the filaments by attachment means that are not shown in the figure.

An element that induces ultrasonic vibrations, for example, can be connected to the floating bar to facilitate the drop in crystals that can be deposited on the filaments (not shown in the figure).

Cylindrical zone B (FIG. 2) comprises a supply (9) of cold gas to the lower part of the chamber, approximately in the vicinity of the lower end of the filaments, and an output (10) of hotter gas that results from the heat exchange with the feedstock under lower wall (2) of supply chamber (40).

Peripheral orifices (11) that are regularly distributed over the periphery make it possible to collect the gas and to evacuate it through output (10) in the direction of the recompression means. The suspension of crystals that are formed by cooling upon contact with the cold gas that circulates in countercurrent to the flow of the film of the feedstock is evacuated through an output (20) that is immersed in decanting zone C that is partially filled with liquid (mother liquor). This zone C has a larger diameter than that of zone B and is approximately concentric.

A fluidtight connection is made between two chambers B and C, with supply (9) of cold gas.

In zone C, the crystals in suspension in the mother liquor are recovered. This zone C for decanting and purification is also a zone for maturation and growth of crystals.

This zone operates, for example, according to a pulsed-column purification system that is described in the "Handbook of Chemical Engineers," Perry, 6th Edition 17, pages 6 and 7.

The combination of an intermittent supply (14) of an added gas ($N_2$, for example) at a higher pressure in the upper part of chamber C above the level of the liquid and cyclic pulsations that result from the introduction of this gas contributes to the decanting and the purification of the crystals. These pulsations also make it possible to keep the crystals in suspension.

The level of the mother liquor can therefore fluctuate in the upper part of chamber C, which has a large enough volume to absorb the variations of the levels of liquid.

A line 49 that is connected to an output (15) that is placed on the periphery of chamber C, located laterally in the upper part of chamber C under the level of liquid, recovers the mother liquor that is produced.

Furthermore, this output (15) is located above the level of output (20) of chamber B, which comes out into chamber C.

A heating bundle (16) that comprises an input and an output of coolant is placed at the bottom of chamber C to melt the crystals that are thus purified. Molten crystals can circulate for an adequate period of time by convection, under the action of a difference in density and owing to induced pulsation movements, from top to bottom and from bottom to top. A portion of the molten phase becomes a reflux which, by contact with the mass of cold crystals relative to the crystallization temperature of the pure paraxylene, is recrystallized and thus purified, while these crystals are reheated and partially melted.

At the lower end of chamber C, an output (17) draws off the purified product, under heating bundle (16).

A system of decanting and purification by pulsed column, whose principle is known but which uses a source of compressed gas (line 23) as a driving fluid, has been described.

At output (20) of chamber B, it would have been possible to introduce the suspension of crystals either into a centrifuge or a rotary filter that makes it possible to separate the crystals of the mother liquor and at the same to wash them or into a countercurrent washing column by molten paraxylene. These purification techniques are described in particular in Patent Applications WO 96/20,908.

According to FIG. 2, a xylene feedstock that is 90% enriched with, for example, paraxylene and that comes from an adsorption process in a simulated fluid bed is sent via a line (41) into a feedstock tank (42).

The liquid feedstock is sent via a pump (43) and a line (44) to a heat exchanger (45) in which it is cooled, and then via line (46) into the upper part of crystallization column (1), from where it flows in the form of film to tubular filaments (5). In its downward movement along the filaments, this film comes into contact in countercurrent with the cold gas that is introduced into the lower part of the column by input (9) which communicates via a line (32) for feeding cold gas and expanded to a turbo-expander (30).

Upon direct contact with the downward-flowing liquid, the cold gas exchanges kilogram calories, reheats, and is evacuated through output (10) and line (22) toward the intake of a compressor (24a) that is put into motion by the turbo-expander. The partially compressed and reheated gas is sent through a line (23) toward the intake of a second compressor (24b) that runs on, e.g., electricity which compresses the gas to an adequate pressure. This compressed gas is introduced via a line (26) toward a heat exchanger (27) with water, which partially cools the compressed gas to a temperature that is compatible with the temperature and the pressure level that are desired at the input of the turbo-expander.

A tank (28) that collects optionally condensed components, for example toluene, can be inserted between the output of exchanger (27) and the input of the turbo-expander. The latter receives the gas which has been cleared of liquid that is condensed by a line (29), connected to the head of tank (28). At the bottom of tank (28), a line (29b) draws off the condensate toward feedstock tank (42).

At the bottom of purification column C, bundle (16) that heats the suspension of crystals is supplied with hot gas by a line (25) where a portion of the compressed and hot gas which comes from compressor (24b) circulates. The cooled gas which comes out of bundle (16) is evacuated via a line (25b) toward the input of heat exchanger (27) and helps to cool the hot compressed gas.

The purified and molten product, paraxylene, is recovered by output (17) at the lower end of chamber c and is drawn off via a line (48).

The mother liquor is recovered at output (15) of chamber C and is drawn off via a line (49) that comprises a pump (32) and heat exchanger (45) that is designed to precool the feedstock at the input of the crystallization chamber. The mother liquor can be recycled at least in part in the column for adsorption of xylenes in a molecular sieve or at least in part in zone A.

Finally, so that the purification column can operate cyclically according to the principle of a pulsed column, a supply (36) of pressurized added gas, connected to line 23, is alternately connected by a rotary valve (33) to column C via line 14 and via line 35 to tank (34) that contains liquid paraxylene and whose bottom is connected to the intake of a pump (50) to line 48.

The following examples illustrate the invention.

A xylene feedstock with 90% paraxylene that comes from adsorption in a simulated fluid bed, on molecular sieve BaX, is considered.

The crystallization process of the invention is brought about according to FIG. 2, with two different temperature levels, whereby the amount of crystallization feedstock per unit of time that is introduced into the crystallization chamber, per ton of paraxylene produced at 99.9% purity, varies with the desired crystallization temperature within the chamber.

EXAMPLE 1

Case where the desired final crystallization temperature is −10° C., whereby the cold gas reaches a temperature of −45° C. at the output of turbo-expander (30).

Amount of feedstock: 1.33 T.

Initial pressure and temperature of the feedstock (line 46): 5 bar abs, 22° C.

Gas flow ($N_2$): 3.85 tons per ton of paraxylene produced.

Output pressure and temperature of the gas of the chamber (line 22): 4.8 bar, +15° C.

Output pressure and temperature of the gas of the compressor (24b) (line 26): 16 bar, 147° C.

Output pressure and temperature of the gas of exchanger (27) (line 29): 15 bar, +30° C.

Pressure and temperature of the gas after expansion (30) (line 31): 5 bar, −45° C.

Power drawn for the recompression of the gas: 142 kW per ton of paraxylene, 47% of which is provided by the turbo-expander to compressor (24a).

Cooling surface area of filaments (5): 60 $m^2$h/ton of paraxylene.

Paraxylene yield: 83.8%.

EXAMPLE 2

Case where the desired crystallization temperature is −50° C., whereby the cold gas reaches a temperature of −70° C. at the output of turbo-expander (30), and whereby gas flow ($N_2$) remains the same as in Example 1.

Amount of feedstock: 1.14 T.

Pressure and temperature of the feedstock (line 46): 5 bar abs., 20° C.

Output pressure and temperature of the gas of the chamber (line 22): 4.8 bar, +10° C.

Output pressure and temperature of the gas of the compressor (line 26): 21 bar, 200° C.

Output pressure [and] temperature of the gas of the exchanger (line 29): 20 bar, 30° C.

Pressure and temperature of the gas after expansion (line 31): 5 bar, −70° C.

Power drawn for the recompression of the gas: 177 kW per ton of paraxylene, 57% of which is provided by the turbo-expander.

Power drawn for the thermal exchanger (27): 65 kW/ton of paraxylene.

Cooling surface area of filaments (5): 123 $m^2$h/ton of paraxylene.

Paraxylene yield: 97%.

It is therefore noted that in the case of Example 2, a smaller amount of feedstock is treated per ton of paraxylene produced, and more energy is recovered in compressor (24a) that is put into motion by the approximately isentropic turbo-expander.

In other words, the amount of additional energy that is necessary for the recompression of the gas that is provided by compressor (24b) is very much the same from one example to the next where a crystallization temperature of −10° C. or −50° C. is reached.

The preceding examples can be repeated with similar success by substituting the generically or specifically described reactants and/or operating conditions of this invention for those used in the preceding examples.

The entire disclosure of all applications, patents and publications, cited above and below, and of corresponding French Application No. 97/07.553 are hereby incorporated by reference.

From the foregoing description, one skilled in the art can easily ascertain the essential characteristics of this invention, and without departing from the spirit and scope thereof, can make various changes and modifications of the invention to adapt it to various usages and conditions

What is claimed is:

1. A device for crystallization of a component from a liquid mixture comprising an elongated chamber (1) having an upper part an intermediate part and a lower part said upper part having means (46) for supplying said liquid mixture, said intermediate part having collecting means (20) for, for withdrawing a suspension of crystals of the component in a mother liquor, and said lower part having means for separation and purification of resultant crystals, means (9) for supplying a cold gaseous fluid into at least one point located below the upper part of the elongated chamber and means (22) located in the upper part of the chamber for drawing off hot gaseous fluid resulting from direct counter-current heat exchange of the cold gaseous fluid with aid liquid mixture, said device also comprising means for shaping a descending flow of the liquid mixture such that the cold gaseous fluid that circulates upward exchanges cold directly with the mixture that is shaped, wherein means (22) for drawing off the hot gaseous fluid are connected to at least one means (24b) for recompression of said hot gaseous fluid, wherein the recompression means has an output connected to at least one heat exchanger (27), wherein the heat exchanger has an output that is connected to a turbo-expander (30), and wherein the turbo-expander has an output connected to means (31) for supplying cold gaseous fluid.

2. A device according to claim 1, in which the means for shaping the descending flow of the mixture comprises at least one spraying means designed to form droplets of the mixture measuring between 50 and 500 microns.

3. A device according to claim 1, in which said chamber comprises a large number of filaments (5) suspended, noncontiguous, and approximately parallel to its longitudinal axis, that are supported by attachment means located in the vicinity of the upper end of the chamber and that occupy approximately the entire section of the chamber.

4. A device according to claim 1, in which the means for suitable shaping of the flow comprises a chamber (40) that communicates with said means (46) for supplying the mixture and that comprise a large number of flow orifices (4a) that are pierced on the lower transverse wall of the chamber and are equal in number to that of filaments (5), whereby each filament passes through an orifice, whereby said chamber contains a volume of mixture such that the height of mixture, in combination with the available flow surface area between the orifice and the filament, makes it possible to wet the filament and to ensure an adequate flow of mixture on the surface of each filament.

5. A device according to claim 3, in which the filaments are hollow and are connected to means (7a) for circulation of the recompressed hot fluid.

6. A device according to claim 4, in which each orifice comprises a non-fluidtight sleeve (4) operating with said chamber and with each filament to carry out the wetting of the filament and to ensure an adequate flow of the mixture on the filament.

7. A device according to claim 3, in which the interaxial distance between two adjacent filaments is equal to at least twice the diameter of the filament.

8. A device according to claim 3, in which means (6) for attaching the filaments are connected to means of vibration.

9. A device according to claim 1, further comprising a compressor (24a) couple to the turbo-expander and inserted between the means for drawing off the hot gaseous fluid and means (24b) for recompression of said fluid.

10. A process for separating paraxylene from a hydrocarbon feedstock that contains aromatic isomers with 8 carbon atoms, comprising conducting said separation in a device according to claim 1.

11. A process according to claim 10, in which the hydrocarbon feedstock that contains said isomers is obtained from an adsorption process on a molecular sieve in a simulated fluid bed or a process for selective dismutation of toluene.

12. A process according to claim 10 comprising expanding the resultant compressed and precooled gas compressing a gas selected from the group consisting of air, hydrogen, nitrogen and helium to an initial pressure and precooling said compressed gas to a temperature T so that the expanded gas has a temperature that is lower by at least 10° C. than temperature T, at its intake into a crystallization zone, the temperature being based on the purity of the hydrocarbon feedstock and the crystallization yield, wherein the hydrocarbon feedstock is introduced into the upper part of the crystallization zone, the cold expanded gas is introduced into at least one point in the lower part of the crystallization zone, the cold expanded gas is brought into direct countercurrent contact with the hydrocarbon feedstock, a suspension of paraxylene crystals is recovered in a mother liquor in the lower part of the crystallization zone, and hot gas is recovered in the upper part of the crystallization zone, the hot gas is recompressed to a pressure, approximately equal to the initial pressure, the resultant recompressed gas is cooled at least in part to temperature T, the crystals of the mother liquor are separated, and the paraxylene crystals are recovered.

13. A process according to claim 12, in which the feedstock is introduced by spraying into the upper part of the crystallization zone in the form of droplets measuring from 50 to 500 microns.

14. A process according to claim 12, in which the crystallization zone comprises a large number of filaments that are suspended, non-contiguous, and approximately parallel to its longitudinal axis, supported by attachment means and occupying approximately the entire section of said zone.

15. A process according to claim 12, in which the hydrocarbon feedstock is introduced into a chamber that comprises a large number of flow orifices that are pierced on its lower wall and are equal in number to that of the filaments, whereby each filament passes through an orifice, and feedstock is made to flow at a controlled rate on each filament in the form of a film into the annular flow space that is available between the orifice and the filament.

16. A process according to claim 14, in which the filaments are hollow and in which a low flow rate of recompressed hot gas is made to pass.

17. A process according to claim 12, in which after recompression the hot gas is cooled between −30 and +70° C., preferably between 20 and 50° C., and then is expanded at a ratio of 1.5 to 5 relative to the initial pressure.

18. A process according to claim 12, in which the pressure of the expanded gas is 1 to 15 bar.

19. A process according to claim 12, in which the crystals are separated from the mother liquor in a centrifuge.

20. A process according to claim 12, in which the crystals are washed in a countercurrent washing column.

21. A process according to claim 12 wherein the temperature is 20 to 50° C. lower.

22. A process according to claim 18 wherein the pressure is 4 to 8 bar.

23. A device according to claim 2, wherein said droplets size is 150 to 200 microns for at least 80% of the droplets.

24. A process according to claim 17, wherein the hot gas is cooled to between 20 and 50°.

25. A device according to claim 1, wherein said means for separation and purification of resultant crystals comprises means for melting the crystals.

26. A process according to claim 12, wherein the crystals of the mother licker are melted and the paraxylene crystals in molten form are recovered.

* * * * *